(12) United States Patent
Esham et al.

(10) Patent No.: US 7,379,531 B2
(45) Date of Patent: May 27, 2008

(54) BEAM THERAPY TREATMENT USER INTERFACE MONITORING AND RECORDING SYSTEM

(75) Inventors: Matthew Paul Esham, Pennsville, NJ (US); Loretta A. Fitzgerald, Collegeville, PA (US); Andrew Chi, King of Prussia, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 259 days.

(21) Appl. No.: 11/392,282

(22) Filed: Mar. 29, 2006

(65) Prior Publication Data

US 2006/0280287 A1    Dec. 14, 2006

Related U.S. Application Data

(60) Provisional application No. 60/690,119, filed on Jun. 13, 2005.

(51) Int. Cl.
*A61N 5/10* (2006.01)
(52) U.S. Cl. .......................................... 378/65; 378/210
(58) Field of Classification Search .................. 378/65, 378/210
See application file for complete search history.

(56) References Cited

U.S. PATENT DOCUMENTS

| 6,393,096 | B1 | 5/2002 | Carol et al. |
| 6,405,072 | B1 | 6/2002 | Cosman |
| 6,853,702 | B2 | 2/2005 | Renner |
| 2002/0188194 | A1 | 12/2002 | Cosman |
| 2003/0219098 | A1 | 11/2003 | McNutt et al. |
| 2004/0096033 | A1 | 5/2004 | Seppi et al. |
| 2004/0122311 | A1 | 6/2004 | Cosman |

(Continued)

OTHER PUBLICATIONS

"TeraRecon to demonstrate National Cancer Institute's 3D radiation treatment software and Aquarius Workstation at ASTRO," http://www.terarecon.com/news/press/2001/10_october_26_pr.html, retrieved Mar. 28, 2006.

(Continued)

*Primary Examiner*—Chih-Cheng G Kao
(74) *Attorney, Agent, or Firm*—Alexander J. Burke

(57) ABSTRACT

A system uses a digital photographic camera attached to a radiation therapy device to create an overlay of radiation beam information comprising data identifying treated patient anatomical region data and supporting determination of cumulative radiation treatment information from multiple treatment overlays. A system records a treatment beam landing area on the anatomical body surface of a patient for use in radiation or other therapy. The system includes an input processor for receiving data representing an image of the surface of a portion of the anatomy of a patient. A data processor provides beam landing position data relative to the image by calculating a position of a treatment beam landing area relative to the image using received input data indicating projection characteristics of a treatment beam used in treating the portion of the anatomy of the patient. A storage processor stores the beam landing position data in a record associated with the patient.

16 Claims, 7 Drawing Sheets

U.S. PATENT DOCUMENTS

2005/0027196 A1* 2/2005 Fitzgerald ............... 600/436
2005/0111621 A1  5/2005 Riker et al.
2005/0143965 A1  6/2005 Failla et al.
2005/0197564 A1  9/2005 Dempsey
2005/0207531 A1  9/2005 Dempsey et al.
2007/0140425 A1* 6/2007 Kamikonya et al. ......... 378/65
2008/0002811 A1* 1/2008 Allison ..................... 378/65

OTHER PUBLICATIONS

"Theragnostic Imaging for radiation oncology: dose-painting by numbers" http://faculty.washington.edu/kinahan/pims/Theragnostic-point.pdf SM Bentzen, The Lancet 6: 112-117, 2005.

* cited by examiner though this is a non-provisional application of provisional application Ser. No. 60/690,119 by M. P. Esham et al. filed Jun. 13, 2005.

FIELD OF THE INVENTION

This invention concerns a system for the recording of a treatment beam landing area on the anatomical body surface of a patient for use in radiation or other therapy.

BACKGROUND OF THE INVENTION

Healthcare workers in a radiology department of a hospital, for example, need to record and document locations (area and volume) on patient anatomy where radiation beam therapy occurs. In existing radiology departments, radiation personnel typically document beam placement using representation diagrams. The radiation personnel also (or alternatively) directly mark patient skin and photograph the marked areas. These diagrammatic representations or photographed hand marked anatomy images are time consuming to produce, potentially inaccurate and fail to provide an electronic digital record. A system according to invention principles addresses this problem and associated problems.

SUMMARY OF THE INVENTION

A system involves a digital photographic camera attached to a radiation therapy device to create an overlay of radiation beam information comprising data identifying treated patient anatomical region data and supporting determination of cumulative radiation treatment information from multiple treatment overlays. A system records a treatment beam landing area on the anatomical body surface of a patient for use in radiation or other therapy. The system includes an input processor for receiving data representing an image of the surface of a portion of the anatomy of a patient. A data processor provides beam landing position data relative to the image by calculating a position of a treatment beam landing area relative to the image using received input data indicating projection characteristics of a treatment beam used in treating the portion of the anatomy of the patient. A storage processor stores the beam landing position data in a record associated with the patient.

DETAILED DESCRIPTION OF THE INVENTION

Figure 1:
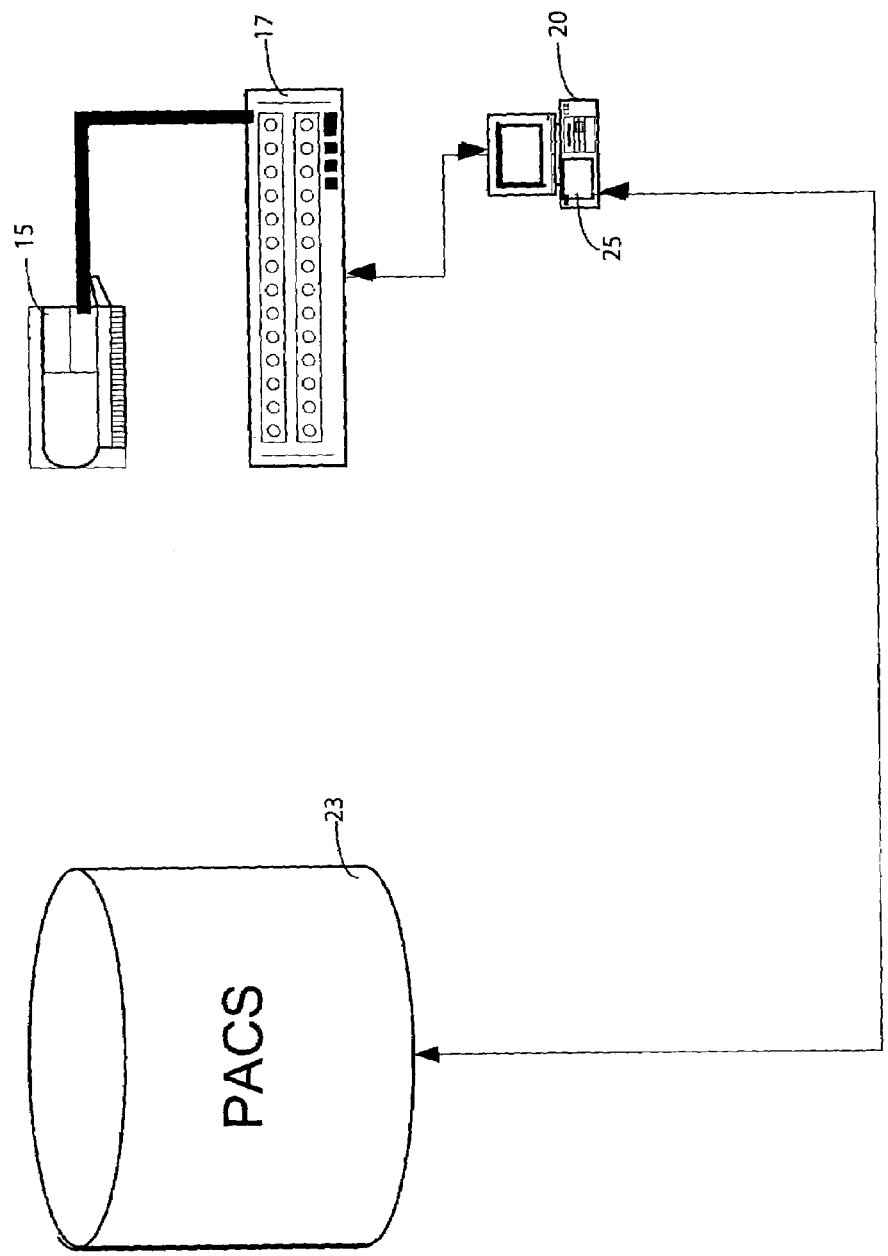
FIG. 1 shows a system for recording a treatment beam landing area on the anatomical body surface of a patient for use in radiation or other therapy, according to invention principles.

A system enables physicists and radiation oncology personnel to accurately store information regarding positioning of a radiation beam and its contact points on the surface of, and within, the anatomy of a patient. A radiation oncologist needs accurate data regarding previous radiation dosage received by a region of patient anatomy in order to determine a current dosage and treatment of a patient and to ensure no single area of tissue is overexposed to radiation. This information is needed in a timely fashion to support seamless oncologist workflow (task sequence) performance. The system enables radiation oncology personnel to accurately view a radiation beam (two dimensional and three dimensional) contact region within a patient without use of subjective, potentially inaccurate drawings. The system employs a digital photographic camera attached to a radiation oncology therapy device used in treating cancer to create an image overlay providing information indicating radiation beam therapy treatments previously received by a patient. The information also indicates associated patient anatomical region data showing anatomical regions (both skin surface and internal three dimensional regions) receiving the treatments.

An executable application as used herein comprises code or machine readable instruction for implementing predetermined functions including those of an operating system, healthcare information system or other information processing system, for example, in response user command or input. A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device. Further, workflow comprises a task sequence for performance by one or a combination of, a healthcare worker, device or software.

The system compiles information from overlays from multiple treatments to determine cumulative radiation treatment of individual anatomical regions over time using an anatomical frame of reference to assure the overlays are accurately positioned on an anatomical image. The anatomical frame of reference to align treatment region overlays may comprise a tattoo a patient receives for radiation targeting purposes, for example. An overlay is stored together with attached data such as Treatment Description and Site identification, Treatment Dates, Field Size, Beam Energy and Modality (i.e. 6 MeV, 10 MeV), Cumulative Dose delivered and patient positioning at time of image capture, for example. The system enables radiation personnel to store data regarding radiation beam placement with minimal additional burden and to store digital images displaying radiation beam placement overlays using standard DICOM compatible archiving functions with the ability to turn a beam overlay on and off. DICOM is a Digital Imaging and Communications in Medicine protocol standard, developed approximately 1990. The system also enables radiology personnel to improve planning of future treatments by viewing composite overlays of previous treatments over a true patient anatomical model (a patient anatomical photograph or image), of treatments performed using the same patient orientation and positioning as used during the radiation therapy. The system documents treatment areas pictorially and in an anatomically correct manner facilitating prevention of overdosing or under dosing of a treatment area.

The system employs a digital imaging camera linked to a radiation treatment device to create composite image data containing anatomical and radiation dosing data stored in DICOM format, e.g., as DICOM compatible secondary capture images with presentation states representing radiation overlay fields, for example. Radiation dosage data is also contained within the DICOM data structure within RT (radiation treatment) image module attributes (tags). A DICOM compatible image study is viewed as an available set of DICOM images of a patient record (in an oncology application, for example). The system takes an anatomical image of a patient during radiation treatment and a record derived using the image is used in the future, when planning further treatment, to indicate actual radiation beam touch down points on the patient body surface. A region of the body may be exposed to a limited cumulative amount of radiation over patient lifetime (there is no half time). Existing systems involve a worker hand drawing with markers an estimated beam touch down area on patient skin and either, transcribing the touch down area to paper, or hand photographing it. In contrast, the system replaces these tasks and creates a composite image data record for future treatment planning so the user can see beam touch down areas on patient skin for treatments that have already occurred so overexposure does not occur through touch down area overlap.

A beam shape is typically a rectangle that can be altered with masks. Whatever the beam shape is, its touchdown area is overlaid (with its coordinates) on a photographic image enabling a user to view the landing area of the actual beam on the patient. The beam is invisible, so the system determines coordinates which are drawn on the skin representing a beam touchdown area so a user can see the beam landing area. An offset distance is also determined and used to calculate beam touchdown area coordinates and compensate for offset distance between a radiation emitter device and a photo camera This is because a camera cannot be placed at the same point as the emitter device and needs to be offset. If, for example, a camera is placed in line, but 6 cm from an emitter device, the coordinates and photograph are shifted 6 cm laterally so the overlay beam landing area is appropriately located.

Figure 3:
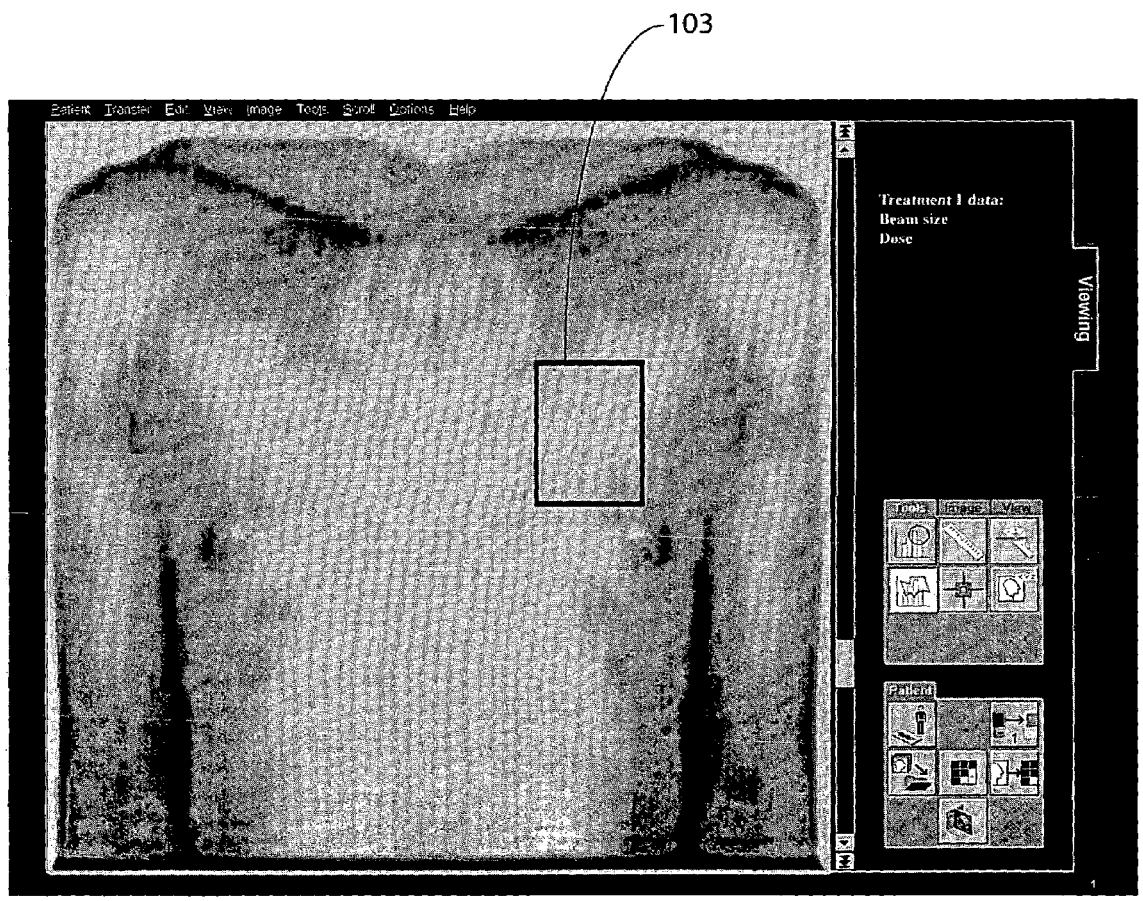
FIG. 3 illustrates superimposition of a radiation therapy beam landing area on a digital anatomical photograph, according to invention principles.

FIG. 1 shows system 10 for recording a radiation treatment beam landing region on the surface of, or within, the anatomy of a patient for use in radiation or other therapy. The patient is set up for radiation treatment. The radiation beam is targeted and applied to the patient, possibly at multiple locations. After each location is treated, a photographic image is taken, and an overlay of the radiation beam is superimposed on this image such that a user can visually see the treatment area. (This functionality enhances existing overlay technologies such as CT, MR, or PET beam overlay functions, to improve a standard task sequence workflow, necessitating radiation treatment personnel hand drawing and photographing beam placement on patient skin). FIG. 3 illustrates superimposition of radiation therapy beam landing area 103 on a digital anatomical photograph of a patient.

A patient is positioned on radiation oncology treatment device 17 (FIG. 1) and the patient position is recorded and entered into DICOM field 0018, 5100. Image overlays with a similar patient position indication are stored and used in compiling composite overlays and radiation dosage associated with multiple treatments over time. System 10 automatically adds the doses of individual treatments of a particular anatomical region identified using DICOM attributes (region and organs affected identification data) and displays the cumulative dosage data as the total dose received. The cumulative dose data is automatically displayed with data acquired for each individual treatment advantageously eliminating the need for a user to determine cumulative dose manually. Multiple views (e.g., AP views in which radiation beams pass from front-to-back (anteroposterior) of a patient chest and associated overlays identifying different beam to skin touch down points of multiple treatments over a period of time, provide information of clinical value.

Figure 6:
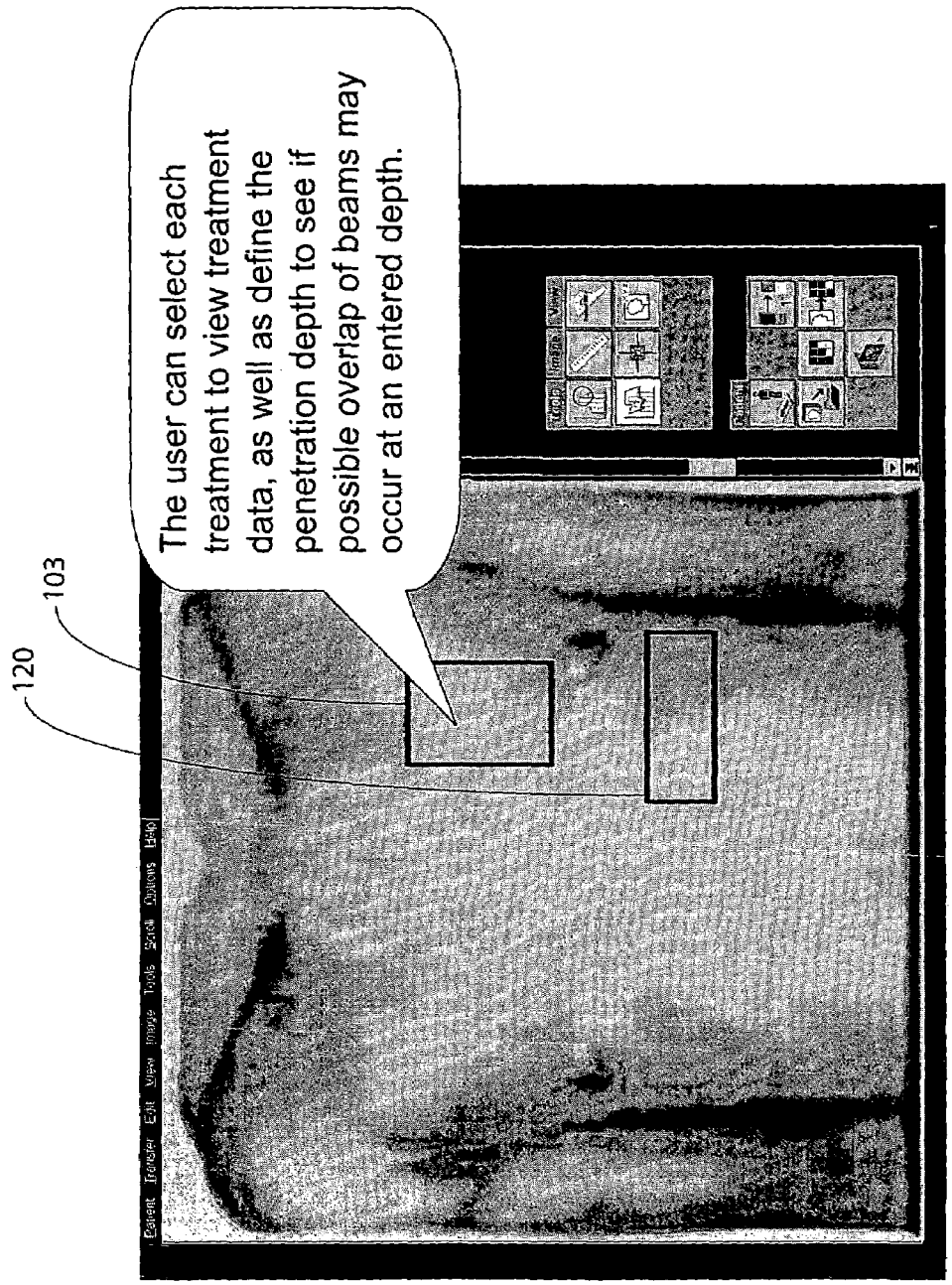
FIG. 6 illustrates superimposition of multiple radiation therapy beam landing areas on a composite digital anatomical photograph to support cumulative treatment determination, according to invention principles.

FIG. 6 illustrates superimposition of multiple radiation therapy beam landing areas on a composite digital anatomical photograph to support cumulative treatment determination. The system superimposes multiple treatments of the same patient position view into a single composite image to enable a user to view overall treatments received by patient anatomy. Radiation therapy beam landing areas 103 and 120 corresponding to different radiation treatments are superimposed on a composite digital anatomical photograph. System 10 automatically combines radiation beam data and anatomical position data and eliminates a need to manually record a beam landing area on patient skin surface and also automatically creates automated links (e.g., hyperlinks) to radiotherapy treatment data for easy retrieval and display of radiation therapy data.

A user employs a user interface in system 10 to select individual treatments in order to view treatment data associated with the selected treatments. The user interface also enables a user to enter desired penetration depths and view beam landing areas at the desired depths to determine if there is beam overlap and increased cumulative radiation received by overlapping areas. In one embodiment, system 10 automatically determines if radiation therapy beams of different treatments overlap at any depth and generates a message for communication to a worker via a display on workstation 20 (or via email, phone or pager, for example) to alert the worker of increased cumulative radiation areas. System 10 automatically adds radiation doses of overlapping beams and displays overlap areas exceeding the allowable dose for an overlapping region of a first beam and a second beam. System 10 also determines overlap areas and excessive dosage and alerts a user of an excessive or other cumulative dosage if the associated treatments are indicated to target different (or substantially similar) anatomical regions. Radiation beam data from radiation oncology treatment device 15 and 17 is superimposed on a photographic image of the patient acquired by a digital camera in unit 15.

Figure 2:
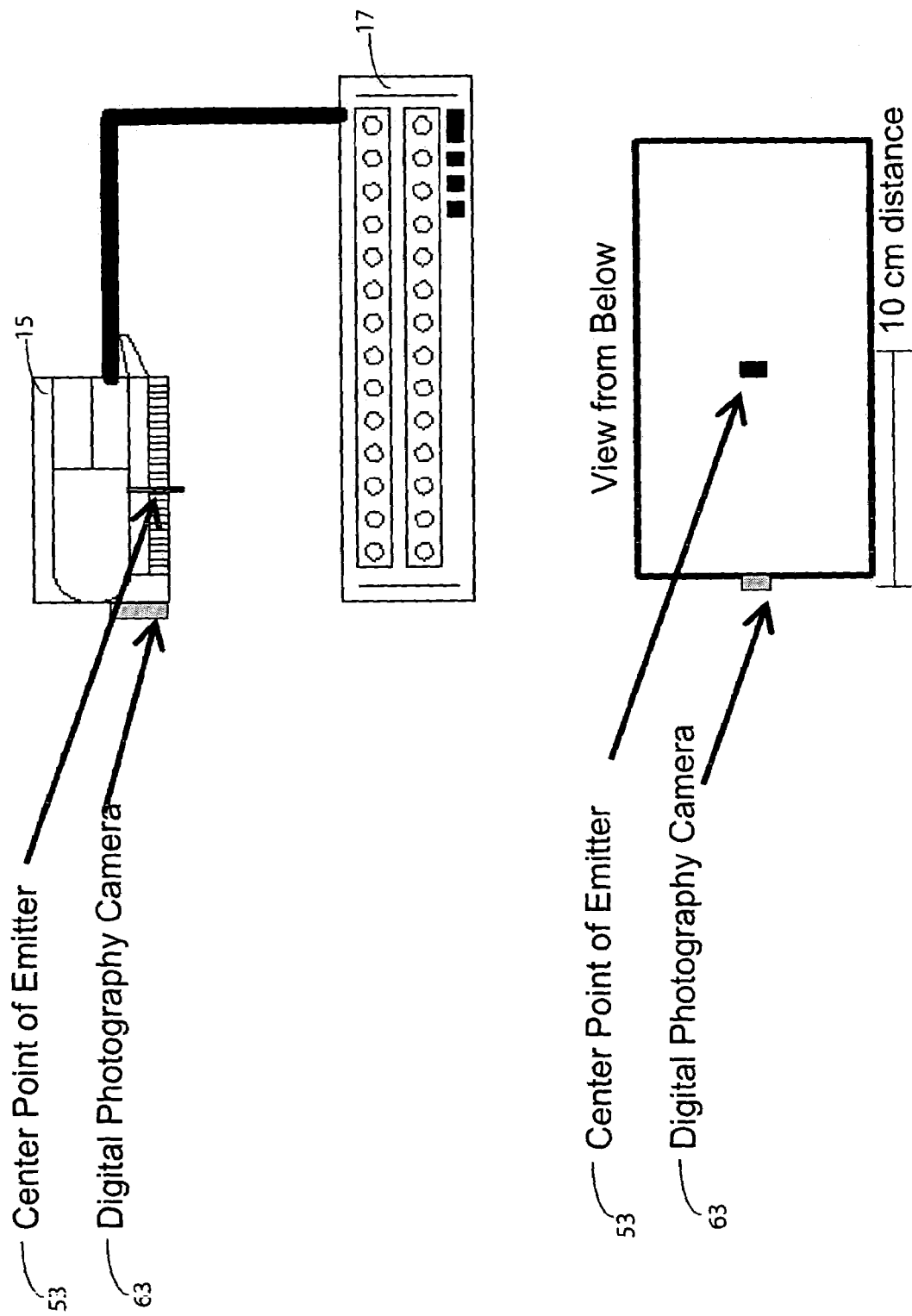
FIG. 2 illustrates camera offset processing in recording a treatment beam landing area, according to invention principles.

FIG. 2 illustrates camera offset processing in recording a treatment beam landing area. The photographic image view is offset by a distance proportional to the distance of the camera axis to the center of the radiation beam to compensate for the distance offset of radiation beam to camera. Thereby system 10 accommodates the 10 centimeter offset distance between the center point 53 of the radiation emitter 15 and the digital camera 63. The system compensates using a configurable offset value to allow the digital camera to be placed on multiple pieces of equipment with different distances from emitter to camera. The center of the emitter is designated as the 0,0 coordinate location, for example and the distance from the camera to the center of the emitter is the offset distance that is to be corrected when creating a beam landing area image overlay. In the sample image, the emitter and the camera are on the same y axis because they are in line; but the x axis is offset by 10 cm. In order to create the overlay, the digital photograph is offset by 10 cm to be correctly superimposed with the beam data.

Radiation treatment data is acquired from treatment device 15 and 17 (FIG. 1) and stored together with image representative digital data, coordinates and other data as overlay data in Picture Archiving Computer System (PACS) repository 23. Multiple treatments for a similar patient position on device 17 are merged and processed by a processor in application 25 executing on workstation 20 (or in a device elsewhere in a network accessed by system 10) to display multiple beam touch down points on a single acquired photographic image. Thereby the photographic image shows a radiation oncologist a pictorial representation of an anatomic relationship of multiple treatment touch down points.

In operation, a patient is positioned on device 17 for radiation treatment. A radiation beam is targeted and applied by emitter 15 to the patient, at one or more anatomical locations. After an individual location is treated, a photographic image is taken by a camera in unit 15, and an overlay of the radiation beam landing area at different anatomical depths is superimposed on this image by a processor in application 25 executing on workstation 20 enabling a user to see the treatment areas superimposed on an anatomical image on workstation 20.

Figure 5:
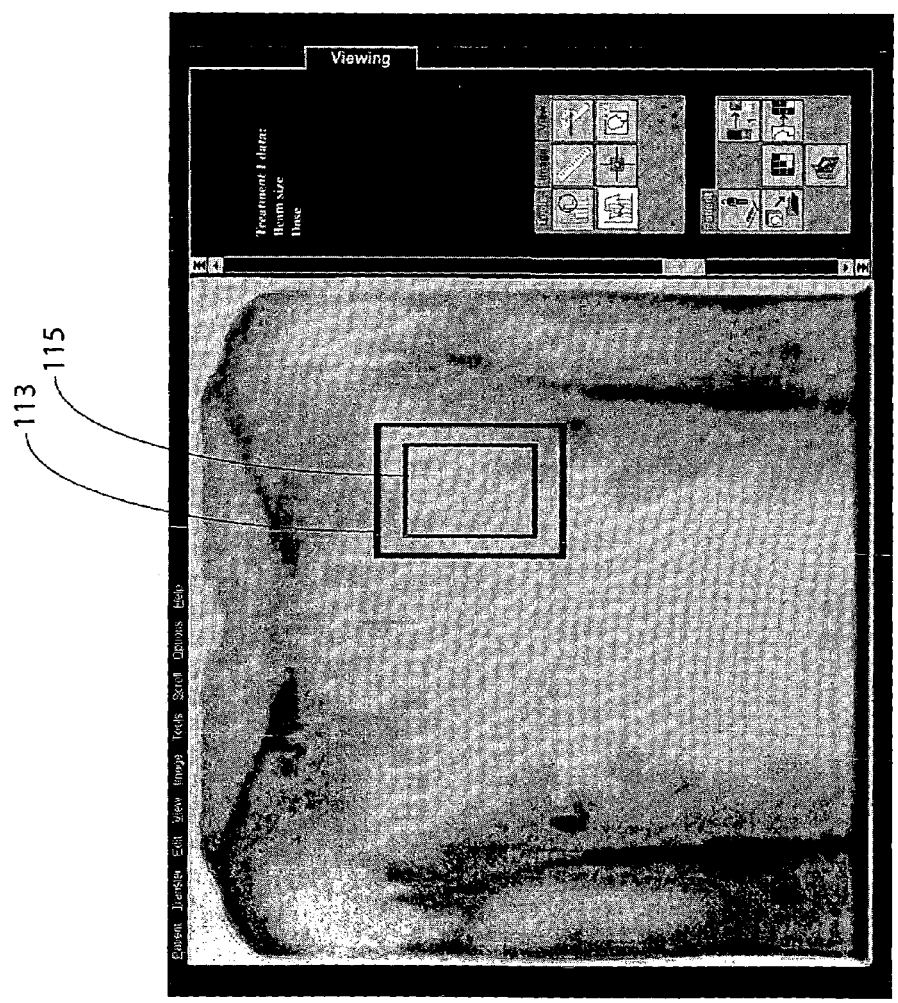
FIG. 5 illustrates radiation therapy beam landing area at different depths superimposed on a digital anatomical photograph, according to invention principles.

FIG. 5 illustrates a radiation therapy beam landing area at different depths superimposed on a digital anatomical photograph. Specifically, it illustrates area 113 on the skin surface of a patient and area 115 at a depth of two centimeters below the skin surface. System 10 provides a user interface enabling a user to select and alter a depth of penetration and to calculate a beam size and landing area at a user selected depth below the skin surface. The user interface displays a shadow box to appear within a surface beam landing area to display the size of the beam and landing area at the selected depth based on the convergence angle of the radiation beam. The system automatically creates the "shadow box" by using a configurable angle of convergence and using the touch down site as a zero depth marker. System 10 automatically calculates a width of a shadow box using the Pythagorean Theorem (PT) to calculate the width of the beam at a selected depth. The system uses the configurable angle of convergence as the angle of the triangle while using the depth as the long edge of the right triangle. The PT is then used to calculate the hypotenuse and the short edge of the triangle. The short edge distance is then added to the beam touch down tracing edge as the shadowbox outline. The long edge is the user entered depth of penetration. The photographic image is used to view the treatment area and the underlying anatomy and comprises a composite image with associated ancillary data enabling multiple radiation treatment areas to be viewed and enabling access to associated treatment information (e.g., in response to user selection of an overlay indicating a treatment area via mouse, mouse over or other user interface action).

Figure 4:
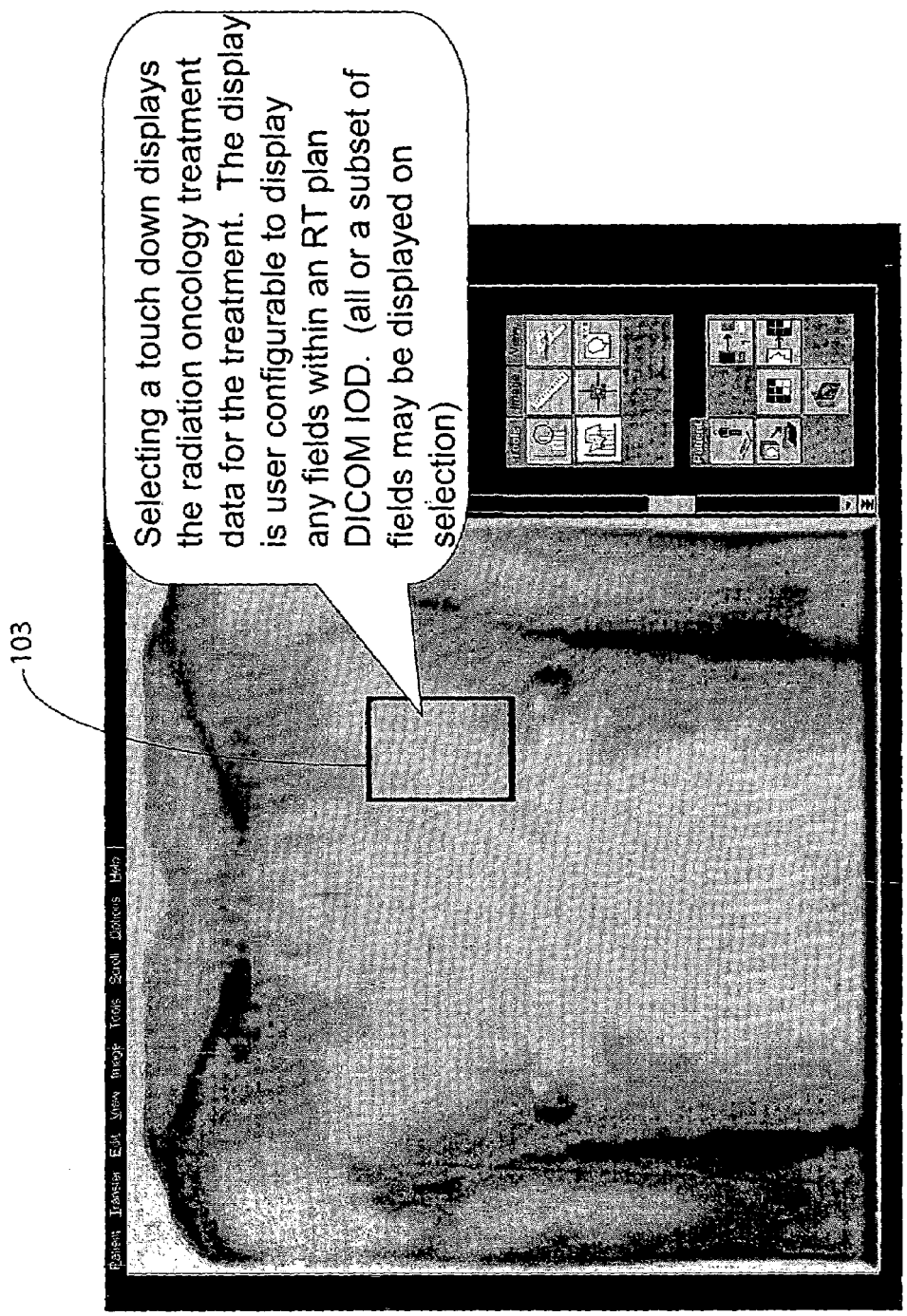
FIG. 4 illustrates recall of stored radiation therapy treatment information upon user selection of an identified radiation therapy beam landing area superimposed on a digital anatomical photograph, according to invention principles.

FIG. 4 illustrates recall and display of stored radiation therapy treatment information upon user selection of identified radiation therapy beam landing area 103 superimposed on a digital anatomical photograph. The treatment information includes, Treatment Description, Field Sizes, Beam Energy, Beam Modality, Cumulative Dose, Daily Dose, Dates Treatment Delivered, and Dose Delivered to Organs at Risk, for example. The display is user configurable enabling display of data fields within a radiation therapy plan DICOM Information Object Definition (IOD) including display of data in the available fields or a subset of the available fields, in response to user selection of area 103. A DICOM IOD is a Data Set comprising a collection of Data Elements stored in a DICOM file. Each DICOM file may or may not include a header consisting of a Preamble and a Prefix and represents a separate class of information. For example, one DICOM file may represent the Computed Tomography Image class, and another DICOM file may represent the Radiotherapy Structure Set class.

System 10 automates a treatment documentation cycle and facilitates accurate treatment data documentation. System 10 also improves radiology treatment care cycles by enabling a user to create a composite image indicating multiple treatments and enabling access to associated treatment information to view a treatment and dosage history in a graphical manner. Existing systems do not provide a photographic image of a specific patient position (as defined by DICOM TAG 0018, 5100 allowable data, for example) comprising a composite image indicating beam landing area on patient skin surface. The system provides advantageous Oncology workflows (worker task sequences). The system facilitates storage of data regarding radiation therapy beam placement with minimal burden and storage of digital images using standard DICOM archive functions and involves a capability to turn display of a radiation beam landing area overlay on and off. The system enables improved planning of future treatments by enabling a user to view composite overlays of previous treatments superimposed on an accurate anatomical model (an anatomical photograph), of radiation therapy treatments performed on a patient in similar patient anatomical position (orientation). The system also documents treatment areas pictorially and in an anatomically correct manner facilitating prevention of overdosing or under dosing of a treatment area and automatically combines radiation beam data and anatomical position data to avoid a need to manually record a beam landing area on patient skin.

System 10 enables radiology oncology personnel to better plan future treatments by viewing composite overlays of previous treatments over a true anatomical model (the underlying photograph), of treatments performed using the same patient positioning. System 10 documents treatment areas pictorially and in an anatomically correct manner and allows a user to view size of a radiation beam at a user determined depth below a patient skin surface. The system allows a user to select a radiation treatment and view data from the treatment together with a total dosage displayed by anatomical region in response to user configured preferences.

Figure 7:
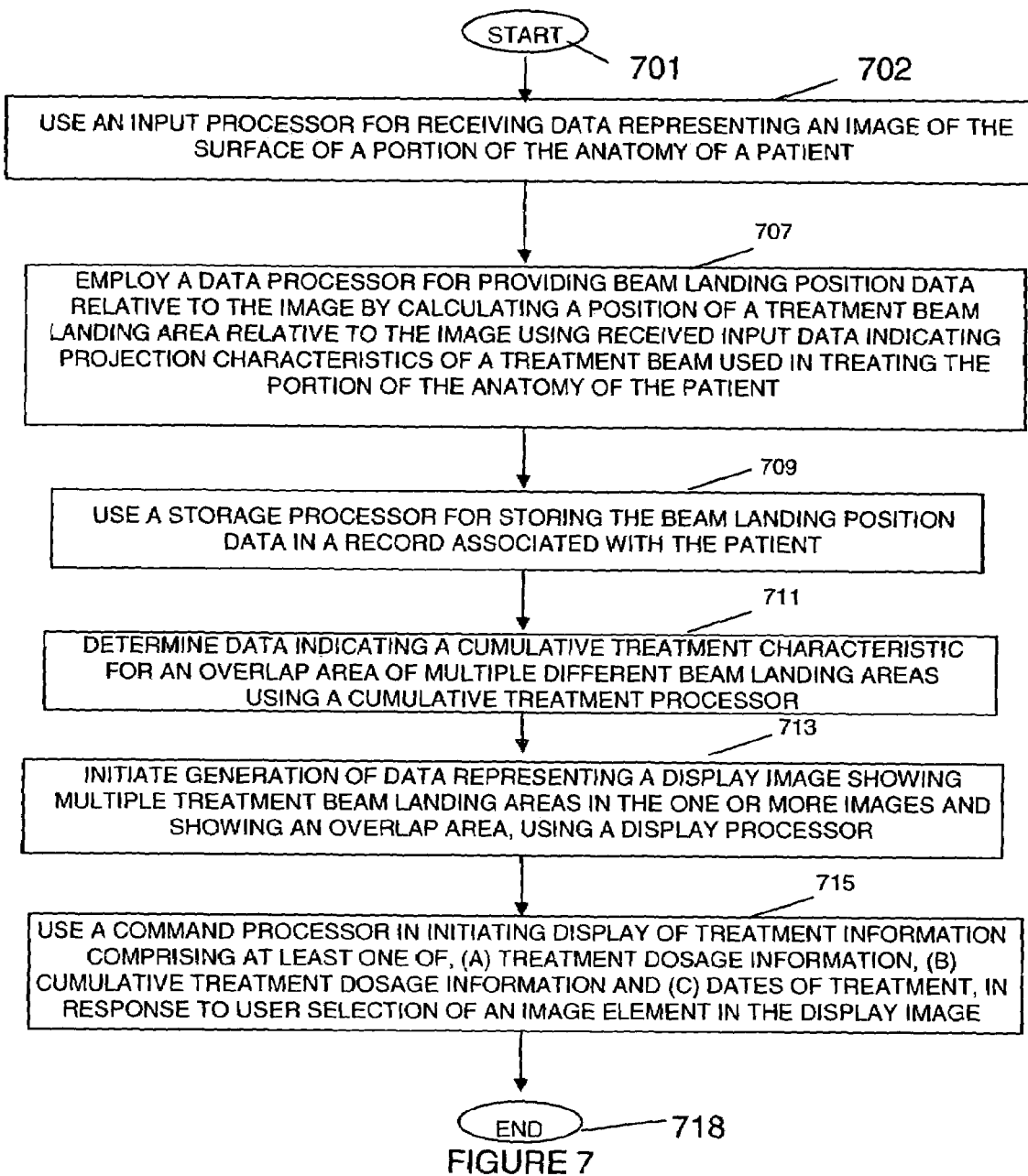
FIG. 7 shows a flowchart of a process employed by a system for recording a treatment beam landing area on the anatomical body surface of a patient, according to invention principles.

FIG. 7 shows a flowchart of a process employed by system 10 including executable application 25 operating on workstation 20, for recording a treatment beam landing area on the surface of, or within, the anatomy of a patient. In step 702, following the start at step 701 an input processor in application 25 receives data, comprising digital data provided by a digital camera, representing an image of the surface of a portion of the anatomy of a patient. The camera is aligned on an axis substantially the same as the axis of the treatment beam or arranged to converge with the treatment beam substantially at a treatment target area of a portion of the anatomy of a patient. In step 707 a data processor in application 25 provides beam landing position data relative to the image by calculating a position of a treatment beam landing area relative to the image. This is done using received input data indicating projection characteristics of a treatment beam used in treating the portion of the anatomy of the patient. The beam landing position data comprises one or more of, Cartesian coordinate data, polar coordinate data and coordinates according to another system. The projection characteristics of the treatment beam comprises data indicating one or more of, treatment beam angle relative to an axis, treatment beam width and treatment beam distance from a beam emitter.

The data processor provides beam landing position data for multiple different beam landing areas associated with corresponding multiple different beam treatments. The beam landing position data for the multiple different beam landing areas is relative to one or more images. The data processor determines a beam landing position data relative to an image using received input data representing an offset between the camera axis through the input lens of the camera and the treatment beam axis. The offset is user configurable to allow positioning of the camera on different items of equipment. The data processor also determines beam landing position data relative to the image at a depth below the surface of the portion of the anatomy of the patient by calculating a position of a treatment beam landing area relative to the image using received input data indicating projection characteristics of a treatment beam used in treating the portion of the anatomy of the patient.

A storage processor in application 25 in step 709 stores the beam landing position data in a record associated with the patient. A cumulative treatment processor in application 25 in step 711 determines data indicating a cumulative treatment characteristic comprising a cumulative radiation dose for an overlap area of multiple different beam landing areas. In step 713 a display processor in application 25 initiates generation of data representing a display image showing the multiple treatment beam landing areas (such as the surface of the portion of the anatomy of the patient) in one or more images and showing the overlap area. In step 715 a command processor in application 25 initiates display of treatment information comprising at least one of, (a) treatment dosage information, (b) cumulative treatment dosage information and (c) dates of treatment, in response to user selection of an image element in the display image. The image element in the display image represents a hyperlink to the treatment information, for example. The command processor also initiates display of treatment information associated with a depth below the surface of a portion of the anatomy of the patient, in response to user selection of an image element in the display image. The process of FIG. 7 terminates at step 718.

The systems and processes presented in FIGS. 1-7 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, any of the functions provided systems and processes of FIGS. 1-7 may be implemented in hardware, software or a combination of both and may reside on one or more processing devices located at any location of a network in the FIG. 1 system or systems attached to the FIG. 1 system.

What is claimed is:

1. A system for recording a treatment beam landing area on an anatomical body surface of a patient for use in radiation or other therapy, comprising:

an input processor conditioned to receive data representing an image of the surface of a portion of the anatomy of a patient;

a data processor conditioned to provide beam landing position data relative to said image by calculating a position of a treatment beam landing area relative to said image using received input data indicating projection characteristics of a treatment beam used in treating said portion of the anatomy of said patient; and a storage processor conditioned to store said beam landing position data in a record associated with said patient.

2. A system according to claim 1, wherein said data representing said image of the surface of said portion of the anatomy of said patient is digital data provided by a digital camera; and said camera is aligned on an axis that is at least one of (a) substantially the same as the axis of the treatment beam, and (b) arranged to converge with the treatment beam substantially at a treatment target area of a portion of the anatomy of a patient.

3. A system according to claim 2, wherein said data processor determines said beam landing position data relative to said image using received input data representing an offset between said camera axis and said treatment beam axis.

4. A system according to claim 3, wherein said offset is user configurable to allow positioning of said camera on different items of equipment.

5. A system according to claim 3, wherein said camera axis is an axis through an input lens of said camera.

6. A system according to claim 1, wherein said data processor determines beam landing position data relative to said image at a depth below the surface of said portion of the anatomy of said patient by calculating a position of a treatment beam landing area relative to said image using received input data indicating projection characteristics of a treatment beam used in treating said portion of the anatomy of said patient.

7. A system according to claim 1, wherein said data processor beam landing position data comprises at least one of (a) Cartesian coordinate data, (b) polar coordinate data, and (c) coordinates according to another system.

8. A system according to claim 1, wherein said data processor provides beam landing position data for a plurality of different beam landing areas associated with corresponding different beam treatments, said beam landing position data for said plurality of different beam landing areas being relative to one or more images.

9. A system according to claim 8, wherein said data processor provides beam landing position data for a plurality of different beam landing areas associated with a corresponding plurality of different beam treatments, said beam landing position data for said plurality of different beam landing areas being relative to one or more images and including a cumulative treatment processor for determining data indicating a cumulative treatment characteristic for an overlap area of said plurality of different beam landing areas.

10. A system according to claim 9, including a display processor for initiating generation of data representing a display image showing said plurality of different beam landing areas in said one or more images and showing said overlap area.

11. A system according to claim 9, wherein said cumulative treatment characteristic comprises a cumulative radiation dose.

12. A system according to claim 1, including a display processor for initiating generation of data representing a display image showing said treatment beam landing area in said image of said surface of said portion of the anatomy of said patient.

13. A system according to claim 12, including a command processor for initiating display of treatment information comprising at least one of (a) treatment dosage information, (b) cumulative treatment dosage information, and (c) dates of treatment, in response to user selection of an image element in said display image.

14. A system according to claim 13, wherein said image element in said display image represents a hyperlink to said treatment information.

15. A system according to claim 12, wherein said data processor determines beam landing position data relative to said image at a depth below the surface of said portion of the anatomy of said patient by calculating a position of a treatment beam landing area relative to said image using received input data indicating projection characteristics of a treatment beam used in treating said portion of the anatomy of said patient and including a command processor for initiating display of treatment information associated with said depth below the surface of said portion of the anatomy of said patient, in response to user selection of an image element in said display image.

16. A system according to claim 15, wherein said received input data indicating projection characteristics of said treatment beam used in treating said portion of the anatomy of said patient comprises data indicating at least one of, (a) treatment beam angle relative to an axis, (b) treatment beam width, and (c) treatment beam distance from a beam emitter.

* * * * *